United States Patent [19]
Riley

[11] Patent Number: 6,017,551
[45] Date of Patent: Jan. 25, 2000

[54] TOPICAL SALVE

[76] Inventor: George E. Riley, 19953 Heyden, Detroit, Mich. 48219

[21] Appl. No.: 09/210,003

[22] Filed: Dec. 11, 1998

Related U.S. Application Data

[60] Provisional application No. 60/069,184, Dec. 11, 1997.
[51] Int. Cl.$^7$ .............................. A61K 7/00; A61K 35/78
[52] U.S. Cl. .................................. 424/401; 424/DIG. 13; 514/783; 514/886; 514/969
[58] Field of Search ............................ 424/401, DIG. 13; 514/886, 969, 783

[56] References Cited

U.S. PATENT DOCUMENTS

| | | | |
|---|---|---|---|
| 4,059,695 | 11/1977 | Hirosaki et al. ........................ | 424/195 |
| 5,073,545 | 12/1991 | Arima et al. ................................ | 514/27 |
| 5,080,901 | 1/1992 | Hangay et al. ........................ | 424/195.1 |
| 5,248,696 | 9/1993 | Bang et al. ............................... | 514/557 |
| 5,470,874 | 11/1995 | Lerner ....................................... | 514/474 |

*Primary Examiner*—Jose' G. Dees
*Assistant Examiner*—Michael A. Williamson
*Attorney, Agent, or Firm*—Weintraub & Brady, P.C.

[57] ABSTRACT

A salve or skin care product for treating discomfort due to burned, inflamed or irritated skin includes a mixture of naturally occurring neutral organic glyceryl esters of fatty acids, such as lard, and small particles of the bark of an Alder tree. The small particles are obtained by pulverized, milling or the like.

5 Claims, No Drawings

TOPICAL SALVE

CROSS REFERENCE TO RELATED APPLICATIONS

This application is a completion application of co-pending U.S. Provisional Patent Application Ser. No. 60/069, 184, filed Dec. 11, 1997 for "Topical Salve", the disclosure of which is hereby incorporated by reference.

BACKGROUND OF THE INVENTION

I. Field of the Invention

The present invention concerns a composition for the treatment of human skin. More particularly, the present invention concerns a topical skin treatment derived from naturally occurring ingredients. Even more particularly, the present invention relates to a composition for the relief and the topical treatment of burned, inflamed, or irritated human skin where the active ingredients are derived form naturally occurring ingredients.

II. Prior Art

As is known to those skilled in the art to which the present invention pertains there is an ever present demand for topical salves for treating irritations and discomfiture caused by burns, inflammations, rashes and the like. Typically, present day salves incorporate synthetic components, such as those disclosed in U.S. Pat. Nos. 5,073,545; 5,248,696 and 5,470,874. An entire class of consumers demands and seeks remedies, such as salves, which are derived solely from naturally occurring components. Thus, the art has also disclosed such compositions as is found in U.S. Pat. Nos. 4,059,695; 5,080,901. It is the quest for further naturally occurring remedial topical salves to which the present invention is directed.

As is disclosed hereinafter the present invention is predicated upon abundant naturally-occurring components which can relieve the discomfiture occasioned by burns, inflammations or irritations.

SUMMARY OF THE INVENTION

The present invention, as detailed below, provides a composition for topically treating the discomfort due to burned, inflamed, or irritated human skin. The skin care product hereof generally, comprises:

(a) naturally occurring neutral organic glyceryl esters of fatty acids;
(b) small particles of the external tissue of the cambium of perennial woody plants of the genus Alnus; and wherein the components are present, in a weight ratio of about 5 to 1 of the (a) to (b) ingredients, respectively.

The source of the esters of fatty acids is, preferably, animal-derived and is, preferably, lard.

Similarly, the bark of an Alder tree is the preferred source of the small particles of a woody plant. The small particles can be obtained through any suitable mechanical treatment of the bark such as by pulverizing or the like.

For a more complete understanding of the present invention reference is made to the following detailed description.

DESCRIPTION OF THE PREFERRED EMBODIMENT

As noted hereinabove, the present invention, provides a composition for topically treating the discomfort due to burned, inflamed, or irritated human skin. The skin care product hereof, which is a salve, generally, comprises:

(a) naturally occurring neutral organic glyceryl esters of fatty acids;
(b) small particles of the external tissue of the cambium of perennial woody plant of the genus Alnus; and wherein the components are present, in a respective weight ratio of about 5 to 1 of the (a) to (b) ingredients.

As is known to those skilled in the art to which the present invention pertains, an ester, denoted by the formula:

$$RCOOR'$$

is a chemical compound formed by the elimination of water and by the bonding of an alcohol and an organic acid, where R may be alkyl or aryl and R' is usually an alkyl radical. Moreover, also as is also known to those skilled in the art which the present invention pertains, an alkyl group is a monovalent radical, of the formula $C_nH_{2n+1}$, which may be considered to be formed by loss of a hydrogen atom from an alkane. Moreover, "n" is a variable taking on non-negative integral values, e.g., 1, 2, 3, 4, etc. Additionally, an aryl is an organic radical derived from an aromatic hydrocarbon by removal of on hydrogen.

Similarly, a glyceryl denoted by the formula:

$$OCH_2OCHOCH_2$$

is known as the functional group from glycerol, having the formula of $(CH_2OH_2)CHOH$. Thus, the glyceryl esters of fatty acids contemplated for use herein, generally, correspond to the glycerol formula.

Esters that are derived from glycerol are known as glycerides. Glycerides, per se, are derived from different carboxylic acids, where such acids are any of the family of organic acids characterized by the presence of one or more carboxyl groups, having a molecular structure as follows:

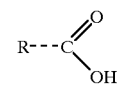

The neutral naturally occurring glyceride esters of fatty acids or glycerides used herein is, preferably, a mixture of $C_{14}$ to $C_{18}$ esters having the following distribution of both saturated and unsaturated acids:

Unsaturated Acids

Enoic

| $C_{14}$ | $C_{16}$ | $C_{18}$ | $>C_{18}$ |
|---|---|---|---|
| 1% | 25-30% | 12-16% | 2-3% |

Dienoic

| $C_{18}$ |
|---|
| 3-8% |

Saturated Acids

| $C_{14}$ | $C_{16}$ | $C_{18}$ |
|---|---|---|
| 1% | 25-30% | 12-16% |

As noted, the glyceryl ester used herein is a naturally occuring fat, as such, it will be a homogeneous mixture of esters of various carboxylic acids.

Such a mixture of glycerides is indigenous to solid fat prepared by rendering the fatty tissue from hogs and is better known as lard. Thus, lard is the preferred glyceryl ester.

As noted below, the second component is derived from a woody plant and, preferably, from the genus Alnus. The tissues located external to the cambium from a perennial woody plant of the genus Alnus as used herein are in the form of small particles. Such small particles may be pulverized or powder particles, obtained by any suitable means such as, but not limited to, milling, grinding, and the likes processes. The tissues located external to the cambium from a perennial woody plant represent, preferably, what is known as the bark of the tree. Representation of the perennial woody plant of the genus Alnus, and what is preferably used herein as a bark source, is the Alder tree.

The present salve is prepared by mixing together, by any suitable means and at ambient conditions, the two components described above, i.e., (a) the naturally occuring neutral glyceryl esters of fatty acids forming (b) the small particles derived from tissues located external to the cambium from a perennial woody plant of the genus Alnus.

In preparing the present composition, the two components are admixed in a weight ratio of at least 1:1 and, preferably, 5:1 of ester to bark The salve is used by topically applying it to the dermal area sought to be treated. Such topical application eases the discomfiture. Because the salve is not water-soluble it remains on the dermis until removed with a suitable agent such as soap.

From the above it is to be readily apparent that there has been described herein a salve for topical application predicated upon all naturally occurring ingredients.

Having, thus, described the invention what is claimed is:

1. A salve for topical application to the skin of the user which comprises:
    (a) naturally occurring neutral organic glyceryl esters of fatty acids;
    (b) small particles of the external tissue of the cambium of perennial woody plants of the genus Alnus,
        wherein the esters and the small particles are present in a respective weight ratio of at least 1:1.

2. The salve of claim 1 wherein the ester and the small particles of woody plants are present in a respective weight ratio of from about 1:1 to about 5:1.

3. The salve of claim 2 wherein the esters and the woody plants are present in a respective weight ratio of about 5:1.

4. The salve of claim 1 wherein the esters comprise lard.

5. A method of topically treating human skin which comprises: (a) topically applying to the skin the composition of claim 1, to relieve the discomfort due to burns, inflammations or irritations.

\* \* \* \* \*